United States Patent [19]

Klahr et al.

[11] Patent Number: 4,479,016

[45] Date of Patent: Oct. 23, 1984

[54] ETHOXYLATES OF DIACETYLENE ALCOHOLS AND THE USE OF THESE COMPOUNDS AS SURFACTANTS

[75] Inventors: Erhard Klahr, Ludwigshafen; Walter Rebafka, Eppelheim; Axel Nissen, Leimen; Wolfgang Trieselt, Ludwigshafen; Albert Hettche, Hessheim, all of Fed. Rep. of Germany

[73] Assignee: BASF Aktiengesellschaft, Ludwigshafen, Fed. Rep. of Germany

[21] Appl. No.: 391,180

[22] Filed: Jun. 23, 1982

[30] Foreign Application Priority Data

Jun. 26, 1981 [DE] Fed. Rep. of Germany ....... 3125109

[51] Int. Cl.$^3$ .............................................. C07C 43/14
[52] U.S. Cl. .................................... 568/606; 568/616; 568/670; 568/673; 568/675; 252/170; 252/351; 252/358; 252/DIG. 1; 424/49
[58] Field of Search ............... 568/606, 616, 670, 675, 568/673

[56] References Cited

U.S. PATENT DOCUMENTS 3,839,465 10/1974 Schneider et al. .................. 568/616

*Primary Examiner*—Howard T. Mars
*Attorney, Agent, or Firm*—Joseph D. Michaels; William G. Conger

[57] ABSTRACT

The invention relates to ethoxylates of diacetylene dialcohols as well as the use of these compounds as surfactants.

9 Claims, No Drawings

ETHOXYLATES OF DIACETYLENE ALCOHOLS AND THE USE OF THESE COMPOUNDS AS SURFACTANTS

BACKGROUND OF THE INVENTION

1. Field of the Invention

The invention relates to ethoxylates of diacetylene dialcohols, as well as the use of these compounds as surfactants.

2. Description of the Prior Art

It is known from *Industrial Engineering Chemistry*, "Product Research Development 4" (1965), pages 236–242, that acetylene alcohols or ethoxylates thereof are low foaming. This publication specifically points out a product group of such compounds which are marketed by Air Reduction Company and which are known under the trade name of SURFYNOL ®.

Such acetylene alcohols and their ethoxylated derivatives are also known from U.S. Pat. No. 3,268,593. The ethoxylates are particularly effective as low foaming surfactants.

From Johnson *The Chemistry of Acetylenic Compounds*, Arnold & Co., London, 1946, Volume 1, pages 227 et seq, diacetylene dialcohols having the following basic structure are known:

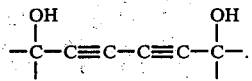

However, this publication does not suggest any technical applications. Neither does this nor subsequent publications suggest that these compounds can be alkoxylated.

For many technical processes, however, the wetting effect and the speed of wetting of these known acetylene derivatives is not yet sufficient. Compounds are needed which exceed the already effective acetylene derivatives as far as the mentioned properties are concerned.

SUMMARY OF THE INVENTION

This invention relates to compositions having the following structural formulae:

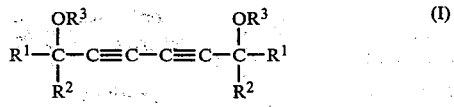

wherein $R^1$ and $R^2$ are individually selected from the group consisting of alkyl radicals having 1 to 10 carbon atoms and $C_5$ or $C_6$ cycloalkyl radicals; and wherein $R^3$ is

wherein n is an integer from 1 to 25. It also relates to the use of these compositions as surfactants having low foaming power.

DESCRIPTION OF THE PREFERRED EMBODIMENT

Familiar processes may be used for the preparation of compounds which are the subject of this invention. As noted, for instance, in *Ber. d. dtsch. Chem. Ges.* (Reports of the German Chemical Society), Volume 69, page 128 et seq, an acetylene-carbinol having the formula

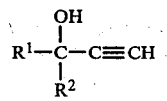

in which $R^1$ and $R^2$ are defined according to Formula I, can be dimerized in an acid medium in the presence of copper(I)-chloride and ammonium chloride while being dehydrogenated, or this dehydrogenating dimerization can be carried out directly with a copper catalyst.

Starting carbinols include the following substances: 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3.

The starting products may initially be ethoxylated which represent the preferred method since the ethoxylate groups are particularly uniformly distributed after the dimerization, that is, since a symmetrical molecule results. On the other hand, however, the operation may also be carried out after the dehydrogenating dimerization since the alcoholic groups have the same reactivity and are thus also uniformly ethoxylated on the average. The latter version is to be preferred with higher degrees of ethoxylation since the dehydrogenation is more difficult to implement if longer ethylene oxide chains are present.

According to this invention 1 to 15 moles of ethylene oxide are used per mole of acetylene alcohol depending upon the intended application. Four to 15 moles of ethylene oxide are used on a preferred basis. The ethoxylation is preferably carried out under the catalytic effect of Lewis acids such as $BF_3$-etherate in a basically known manner. The resultant products may be identified by iodine color number, cloud point, and IR- and carbon/hydrogen-analysis.

The acetylene alcohols and the ethoxylated derivatives have excellent surface active properties and are particularly usable as wetting agents, cleaning agents and/or detergents, and for the manufacture of water-soluble nonionic washing and cleaning agents, toilet soaps, and shampoos since they greatly reduce the surface tension of aqueous solutions. Moreover, they have a high wetting activity which exceeds the values which heretofore were achieved with previous monoacetylene derivatives. Furthermore, it has unexpectedly been found that the presence of two adjacent triple bonds in the hydrophobic chain of the compounds increases the water solubility and improves the surface active properties.

The alkanol-ethylene oxide adducts according to this invention do not have an unpleasant odor, do not have an irritating effect upon the skin, and cause essentially no discolorations when used in mixtures of washing agents. The adducts are either liquids or low melting solids. A particularly advantageous property of the adducts is the fact that they have low foaming power. Therefore, they are particularly well suited for the preparation of toothpastes, mixtures of washing agents for laundry purposes, and other products in which value is placed on low foaming properties. The particularly low surface tension also renders these products usable for technical purposes in which high emulsification properties are demanded.

The substances according to this invention may be used, for instance, in emulsion polymerization processes resulting primarily in the dispersion and in the preparation of secondary polymer dispersions. By being able to vary the number of added ethylene oxide groups in the defined range, it is also possible to use these preparations as emulsifiers as well as demulsifiers.

Finally, the new products are capable of synergistically increasing the effects of other commonly used surface active substances if added to these substances in small amounts. Thus, for instance, amounts of 0.1 to 10 percent, based on the weight of other normally used nonionic surfactants, can be added to a washing or rinsing liquor resulting in a greatly increased washing or cleaning effect.

Since the substances have a definite surface active effect when used on metal surfaces, they may also be added to process solutions that are used for finishing metal surfaces, for instance, in the electrodeposition of heavy metals, such as nickel, where these agents are used as brighteners.

The Examples below are used to explain the invention.

EXAMPLES

General Instructions

One mole of diacetylene alcohol was heated to 50° C. to 100° C. and mixed with 0.2 percent by weight of $BF_3$-etherate as catalyst. At the same temperature, the desired amount of ethylene oxide was added dropwise within a period of two to five hours and the mixture was stirred at 50° C. to 150° C. for one hour. Certain quantities of unreacted ethylene oxide were thereupon removed by distillation.

The resultant product was light yellow to dark yellow and liquid.

EXAMPLE 1

(3,8-dimethyldeca-4,6-diyne-3,8-diol+8EO*)

*EO=ethylene oxide

In a reaction vessel, 194 grams of 3,8-dimethyldeca-4,6-diyne-3,8-diol were heated to 80° C. to 90° C. and were mixed with one milliliter of $BF_3$-etherate. At the same temperature, 355 grams of ethylene oxide were added dropwise within a period of four hours and the mixture was stirred at 80° C. to 90° C. for two hours.

Following this process, small quantities of unreacted ethylene oxide are removed by distillation. The following data were derived from the sample:

Yield: 546 grams
IR (Film): 3410 (OH), 2800 (C—H), 2150 (C≡C), 1100 cm¹ (C—O—)

|  | C | H |
|---|---|---|
| Calculated: | 61.5 | 9.2 |
| Found: | 61.4 | 9.3 |

Elementary Analysis:
Cloud Point $H_2O$: <0° C.
Iodine Color No.: >1100

EXAMPLE 2

[1,4-bis(1-hydroxycyclohexyl)buta-diyne-1,3+8EO]

In a reaction vessel, 232 grams of 1,4-bis(1-hydroxycyclohexyl)buta-diyne-1,3 are heated to 140° C. to 160° C. and mixed with one milliliter $BF_3$-etherate. At the same temperature, 355 grams of ethylene oxide were added dropwise within four hours and the mixture was stirred at 150° C. for two hours.

Subsequently small quantities of unreacted ethylene oxide are removed by distillation. The data derived from the sample were as follows:

Yield: 582 grams dark yellow liquid
IR (Film): 3420 (OH), 2930, 2860 (C—H), 2220 (C≡C) 1120 cm¹ (C—O—).

|  | C | H |
|---|---|---|
| Calculated: | 64.2 | 9.0 |
| Found: | 64.0 | 8.9 |

Elementary Analysis:
Cloud Point $H_2O$<0° C.
Iodine Color No.: >>1100

EXAMPLE 3

(2,6,11,15-Tetramethylhexadecadiyne-7,9-diol-6,11+8EO)

In a reaction vessel, 312 grams of 2,6,11,15-tetramethylhexadecadiyne-7,9-diol-6,11 were heated to 60° C. to 70° C. and were mixed with one milliliter of $BF_3$-etherate. At the same temperature, 355 grams of ethylene oxide were added dropwise within four hours and the mixture was stirred at 60° C. to 70° C. for two hours.

Subsequently small amounts of unreacted ethylene oxide are removed by distillation. The data derived from the sample were as follows:

Yield: 664 grams light yellow liquid
IR (Film): 3430 (OH), 2880 (C—H), 2150 (C≡C), 1120 cm¹ (C—O—).

|  | C | H |
|---|---|---|
| Calculated: | 65.6 | 10.0 |
| Found: | 65.5 | 10.1 |

Elementary Analysis:
Cloud Point $H_2O$: <0° C.
Iodine Color No.: 24.

EXAMPLE 4

(2,6,11,15-Tetramethylhexadecadiyne-7,9-diol-6,11+12EO)

Example 3 was duplicated except with 535 grams of ethylene oxide. The data derived from the sample were as follows:

Yield: 838 grams light yellow product
IR (Film): 3430 (OH), 2870 (C—H), 2140 (C≡C), 1100 cm¹ (C—O—).

|  | C | H |
|---|---|---|
| Calculated: | 63.3 | 9.8 |
| Found: | 63.2 | 9.8 |

Elementary Analysis:
Cloud Point $H_2O$: approximately 10°–15° C.
Iodine Color No.: 24.

APPLIED TECHNOLOGICAL TESTS

The products obtained according to Examples 1 through 4 and the corresponding nonethoxylated basic substances were tested according to DIN 53914 as far as their surface and/or interface activities are concerned, according to DIN 53902 as far as their foaming behavior is concerned and according to DIN 53901 as far as their wetting capacity is concerned. They were compared with the corresponding monoacetylene alcohols. The results are shown in the following Table.

TABLE

| Product | Surface Test 0.01% Aqueous Solution | Interface Test (0.01% Aqueous Solution Compared with Nujol) | Interface Test (0.01% Aqueous Solution Compared with Water) | Foam | Wetting Capacity |
|---|---|---|---|---|---|
| Example 1 | 46.8 | 15.8 | 30.5 | 0 | >300 |
| 3-Methylpentyne-1-ol-3 | 70.3 | 42.7 | 44.5 | 0 | >300 |
| 3-Methylpentyne-1-ol-3 + 4EO | 59.1 | 29.0 | 35.0 | 0 | >300 |
| Example 2 | 54.3 | 19.4 | 33.8 | 0 | >150 |
| Example 2 (not ethoxylated) | 48.8 | 32.4 | 39.1 | 0 | >300 |
| 1-Hydroxy-1-Ethynyl-cyclohexane | 65.3 | 36.1 | 44.7 | 0 | >300 |
| 1-Hydroxy-1-Ethynyl-cyclohexane + 4EO | 56.4 | 25.3 | 35.9 | 0 | >300 |
| Example 3 | 28.5 | 5.5 | 13.1 | 20 | 90 |
| Example 4 | 29.4 | 6.6 | 27.5 | 20 | 21 |
| Example 3 and/or 4 (not ethoxylated) | 38.9 | 33.4 | 30.2 | 0 | 48 |
| 3,7-Dimethyloctyne-1-ol | 53.3 | 35.7 | 43.4 | 0 | 100 |
| 3,7-Dimethyloctyne-1-ol + 4EO | 35.7 | 18.6 | 31.1 | 0 | 80 |
| 3,7-Dimethyloctyne-1-ol + 6EO | 36.1 | 14.3 | 29.0 | 0 | 22 |
| 3,7-Dimethyloctyne-1-ol (not ethoxylated) | 58.2 | 30.5 | 40.6 | 0 | >300 |

EO stands for ethylene oxide

The embodiments of the invention in which an exclusive privilege or property is claimed are defined as follows:

1. A composition of matter having the structural formula:

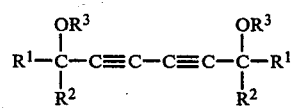

wherein $R^1$ and $R^2$ are individually selected from the group consisting of alkyl radicals having 1 to 10 carbon atoms and $C_5$ or $C_6$ cycloalkyl radicals; and wherein $R^3$ is $-(-CH_2CH_2O-)_n-H$ wherein n is an integer from 1 to 25.

2. The composition of claim 1 which is prepared by dimerizing a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by oxyethylation with from 2 to 50 units of ethylene oxide.

3. The composition of claim 1 which is prepared by dimerizing a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by oxyethylation with from 2 to 30 units of ethylene oxide.

4. The composition of claim 1 which is prepared by dimerizing a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by oxyethylation with from 8 to 30 moles of ethylene oxide.

5. The composition of claim 1 which is prepared by oxyethylating with from 1 to 25 moles of ethylene oxide, a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by dimerization.

6. The composition of claim 1 which is prepared by oxyethylating with from 1 to 15 moles of ethylene oxide, a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by dimerization.

7. The composition of claim 1 which is prepared by oxyethylating with from 4 to 15 moles of ethylene oxide, a compound selected from the group consisting of 3-methylpentyne-1-ol-3, 3,7-dimethyloctyne-1-ol-3, 1-hydroxy-1-ethynyl-cyclohexane, 3-ethylpentyne-1-ol-3, 3-methylhexyne-1-ol-3, and 3-methylbutyne-1-ol-3, followed by dimerization.

8. The composition of claim 1 wherein n is an integer from 1 to 15.

9. The composition of claim 1 wherein n is an integer from 4 to 15.

* * * * *